US011416064B2

(12) United States Patent
 Naik (10) Patent No.: US 11,416,064 B2
(45) Date of Patent: Aug. 16, 2022

(54) ALERTS WITH AUGMENTED REALITY

(71) Applicant: Siemens Healthcare Diagnostics Inc., Tarrytown, NY (US)

(72) Inventor: Sandeep M. Naik, Bridgewater, NJ (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 0 days.

(21) Appl. No.: 16/607,799

(22) PCT Filed: May 16, 2018

(86) PCT No.: PCT/US2018/032903
 § 371 (c)(1),
 (2) Date: Oct. 24, 2019

(87) PCT Pub. No.: WO2018/213400
 PCT Pub. Date: Nov. 22, 2018

(65) Prior Publication Data
 US 2020/0192465 A1 Jun. 18, 2020

Related U.S. Application Data

(60) Provisional application No. 62/507,424, filed on May 17, 2017.

(51) Int. Cl.
 *G06F 3/01* (2006.01)
 *G06T 7/73* (2017.01)
 (Continued)

(52) U.S. Cl.
 CPC ............ *G06F 3/011* (2013.01); *G06F 3/0488* (2013.01); *G06F 3/04815* (2013.01); *G06T 7/74* (2017.01);
 (Continued)

(58) Field of Classification Search
 CPC .... G06F 3/011; G06F 3/04815; G06F 3/0488; G06T 7/74; G06T 19/006; G06T 2215/16;
 (Continued)

(56) References Cited

U.S. PATENT DOCUMENTS 6,317,127 B1 11/2001 Daily et al.
7,467,187 B2 12/2008 Hesselink et al.
(Continued)

FOREIGN PATENT DOCUMENTS

CA 2777693 1/2013
WO 2013170204 11/2013

OTHER PUBLICATIONS

International Search Report for PCT/US2018/032903 dated Jul. 23, 2018.
(Continued)

*Primary Examiner* — YuJang Tswei (57) ABSTRACT

Disclosed herein is a method of enabling supervision of a laboratory environment utilizing diagnostic equipment. The method includes utilization of a device for capturing an optical image of at least a portion of the laboratory environment. The method further requires selectively capturing the optical image using the image capture device and selectively transmitting the captured image over a communications medium. The method further requires receiving the transmitted optical image by an image receiver in communication with the image transmission device via the communications medium. The method then requires selectively generating, by an image processor in communication with the image receiver, a display of at least a portion of the captured optical image on an image display device and receiving status information from the diagnostic equipment at a laboratory manager that is in communication with multitude of diagnostic equipment.

16 Claims, 5 Drawing Sheets

(51) Int. Cl.
 *G06F 3/04815* (2022.01)
 *G06F 3/0488* (2022.01)
 *G06T 19/00* (2011.01)
 *G06V 20/20* (2022.01)

(52) U.S. Cl.
 CPC ............ *G06T 19/006* (2013.01); *G06V 20/20* (2022.01); *G06T 2215/16* (2013.01)

(58) Field of Classification Search
 CPC .... G06K 9/00671; G16H 10/40; G16H 40/60; G16H 40/20; G16H 40/40
 See application file for complete search history.

(56) References Cited

U.S. PATENT DOCUMENTS

| | | | | |
|---|---|---|---|---|
| 8,273,022 | B2* | 9/2012 | Say | A61B 5/01 |
| | | | | 600/365 |
| 8,648,910 | B2 | 2/2014 | Heydlauf | |
| 2005/0210330 | A1 | 9/2005 | Platteter | |
| 2010/0037169 | A1* | 2/2010 | Beaty | G06F 11/324 |
| | | | | 715/772 |
| 2010/0050116 | A1* | 2/2010 | Blick | G16H 10/40 |
| | | | | 715/833 |
| 2011/0099430 | A1* | 4/2011 | Lloyd | G06F 11/3495 |
| | | | | 714/43 |
| 2012/0299928 | A1 | 11/2012 | Shikhman | |
| 2013/0024381 | A1* | 1/2013 | Dala | G06Q 10/00 |
| | | | | 705/51 |
| 2014/0000659 | A1 | 1/2014 | Biliner et al. | |
| 2014/0257698 | A1* | 9/2014 | Jo | H04M 3/42 |
| | | | | 701/538 |
| 2015/0356786 | A1 | 12/2015 | Bare et al. | |
| 2016/0020986 | A1* | 1/2016 | Bosko | G16H 40/67 |
| | | | | 709/224 |
| 2016/0140868 | A1 | 5/2016 | Lovett et al. | |
| 2016/0173816 | A1 | 6/2016 | Huenerfauth et al. | |
| 2016/0260326 | A1* | 9/2016 | Ng-Thow-Hing | G02B 27/01 |
| 2016/0314621 | A1* | 10/2016 | Hill | G06T 7/73 |
| 2016/0378950 | A1* | 12/2016 | Reiner | G16H 10/60 |
| | | | | 705/2 |
| 2017/0091607 | A1 | 3/2017 | Emeis et al. | |
| 2017/0103137 | A1* | 4/2017 | Lawson | G05B 11/01 |
| 2017/0323481 | A1* | 11/2017 | Tran | G06F 19/00 |
| 2018/0089870 | A1* | 3/2018 | Billi-Duran | G06T 11/60 |

OTHER PUBLICATIONS

International Preliminary Examination Report PCT/US2018/032903 dated Sep. 19, 2019.

* cited by examiner

ALERTS WITH AUGMENTED REALITY

RELATED APPLICATIONS

This application claims the benefit of priority of U.S. Application No. 62/507,424 filed on May 17, 2017.

TECHNICAL FIELD

The disclosure herein relates generally to an implementation of a 3D view of a laboratory process manager in combination with augmented reality technology to allow laboratory processing alerts to be overlaid on top of the live feed and thereby facilitating a user's interaction with the alerts.

BACKGROUND

Laboratories are a fundamental source of scientific evidence critical for clinical research and decision making in clinical diagnostics and patient care. The use of clinical laboratory test results in diagnostic decision making is an integral part of clinical medicine. The menu of laboratory tests available to clinicians constitutes an impressive array that has expanded exponentially since the first useful analytical tests were developed. The current list of tests offered by at least one major reference laboratory includes nearly 3,000 analytes, which does not include the additional array of more commonly ordered tests (e.g., complete blood count [CBC], electrolytes [sodium, potassium, chloride, carbon dioxide], thyroid stimulating hormone [TSH], glucose, etc.) routinely performed on site by most hospital-based clinical laboratories.

Automation, broadly defined, is the mechanization of the steps in a procedure. Through mechanization of analyses there is increased reproducibility of results. Automation allows a reduction of human error and laboratory expenses, which are important in these economic times, as laboratories are challenged with budgetary constraints.

Since the early days of laboratory automation, continuous scientific and technological advances as well as developments in robotics and information technology have led to the introduction of the wide range of automated analyzers currently in the market, which can be applied to different working laboratory environments. Though automation reduces the hands-on intervention and the time needed to set up, run, and analyze results, human intervention is often times still required for loading/unloading, operation, and instrument maintenance, as well as for the interpretation of results.

The introduction of automation in clinical chemistry leads to a higher volume of testing and faster turnaround time. Most automated systems contain software that schedules the order in which the instrument performs pending tasks. Tests to be performed are entered on a keyboard requested for either routine tests or emergency (STAT) tests. The software monitors the status of the system during testing. The provision of kits, including the reagents needed to perform the analysis, ready-to-use or requiring minimal preparation, as well as the instructions for use, further facilitate the testing process. The analytical instruments can be fully or semi-automated, large floor or benchtop models, open or closed systems. The technological/scientific innovations which pave the way for the development of current automated analyzers are rapidly advancing.

Continuous scientific and technological advances, as well as developments in robotics and information technology, led to the introduction of the wide range of automated analyzers currently in the market. Automation in a laboratory provides increased precision, reproducibility, and throughput. It also reduces human error and laboratory expenses and facilitates the allocation of human resources: laboratory personnel are freed from time-consuming, repetitive tasks. The level of automation required and the choice of the automated analyzers depends on the needs and resources of the laboratory.

Automated analyzers efficiently assist laboratory professionals. However, the human factor is still important in the process, going from the decision to automate operations to the interpretation of the test results, with the aim of using this information to improve outcomes in different laboratory testing applications.

An example of software customizable for process management solution that enables laboratories to oversee process data for their automation system, IT and connected instruments-thus simplifying management of day-to-day laboratory tasks is the Atellica™ PM 1.0 software for simplified lab operations. The software enables labs to develop a central 3-D control panel for laboratory personnel to monitor and navigate all connected systems without physically walking from system to system. To further streamline lab operations, the software tracks levels of onboard reagents and consumables, alerting operators of low-consumable levels in real-time.

The Atellica™ PM 1.0 Software simplifies laboratory operations, enabling laboratory technicians to spend less time on process-related tasks. The Atellica™ software centralizes all instrument data onto one screen. With the Atellica™ software, designated operators can customize alerts, dashboards, and priority sample rules, as well as manage sample and workflow exceptions. The software can be configured so that operators can access the software simultaneously with customized settings based on their specific responsibilities. They can also view different laboratories, locations, or sites. The software's reporting features enable real-time assessment of key metrics such as turn-around times, testing volumes, or more specific management goals—eliminating the need to export data to another platform.

Identifying the precise location of the alert, such as a low reagent, within a large clinical laboratory remains an area in need of further attention. Because many of the clinical laboratories contain a large number of analytical devices, spread out over possibly many thousands of square feet, simply obtaining an alert that a reagent supply may be low does not necessarily provide sufficient detail to allow a laboratory worker to expeditiously address the alert. What is needed is a method of enabling supervision of a laboratory environment containing multiple diagnostic devices that marries existing process management software with virtual reality capabilities thereby allowing a laboratory worker to immediately proceed to the location of the alert and to rectify any component concern.

SUMMARY

A medical laboratory is a complex system and all aspects must function properly to achieve the requisite quality. Laboratory quality can be defined as accuracy, reliability, and timeliness of the reported test results. The laboratory results must be as accurate as possible, all aspects of the laboratory operations must be reliable, and reporting must be timely in order to be useful in a clinical or public health setting. Laboratories produce test results that are widely used in clinical and public health settings, and health outcomes depend on the accuracy of the testing and reporting. If inaccurate results are provided, the consequences can be very significant, including: unnecessary treatment; treatment complications; failure to provide the proper treatment; delay in correct diagnosis; and additional and unnecessary diagnostic testing. These consequences result in increased cost in time, personnel effort, and often in poor patient outcomes.

In order to achieve the highest level of accuracy and reliability, it is essential to perform all processes and procedures in the laboratory in the best possible way. The laboratory is a complex system, involving many steps of activity and many people. The complexity of the system requires that many processes and procedures be performed properly. Therefore, the quality management system model, which looks at the entire system, is very important for achieving good laboratory performance.

There are many procedures and processes that are performed in the laboratory and each of these must be carried out correctly in order to assure accuracy and reliability of testing. An error in any part of the cycle can produce a poor laboratory result. A method of detecting errors at each phase of testing is needed if quality is to be assured. The complexity of the laboratory system requires that many factors must be addressed to assure quality in the laboratory. Some of these factors include: the laboratory environment; quality control procedures; communications; record-keeping; competent and knowledgeable staff; good quality reagents and equipment.

Disclosed herein is a laboratory monitoring apparatus with an augmented video display for use with a laboratory environment having a plurality of diagnostic equipment. The monitoring apparatus includes an image capture device for selectively capturing an optical image of at least a portion of the laboratory environment as well as an image transmission device, in communication with the image capture device, for selectively transmitting the captured optical image over a communications medium. The laboratory monitoring apparatus includes an image receiver that is in communication with the image transmission device via the communications medium, for receiving the transmitted optical image from the image transmission device as well as an image display device, and an image processor in communication with the image receiver and the image display device. The imager receiver is for selectively generating a display of at least a portion of the captured optical image on the image display device.

The laboratory monitoring apparatus disclosed herein also includes a laboratory manager in communication with the plural diagnostic apparatus at least for receiving status information therefrom and for selectively directing the image processor to embed a rendered graphical element within the generated display in response to the status information. The graphical element is for communicating status information regarding one or more of the plural diagnostics apparatus within the laboratory environment to a user viewing the display on the image display device.

It is an object of the laboratory monitoring apparatus disclosed herein to comprehensively visualize the laboratory and alerts that can expeditiously draw attention to areas of the laboratory that are experiencing problems.

It is a further object of the laboratory monitoring apparatus disclosed herein to improve the association of the laboratory alerts with the respective area for quicker assessment by the operator.

These, together with other aspects of the disclosed laboratory monitoring apparatus along with the various features of novelty that characterize the technology, are pointed out with particularity in the claims annexed hereto and form a part of this disclosed technology. For a better understanding of the disclosed technology, its operating advantages and the specific objects attained by its uses, reference should be made to the accompanying drawings and descriptive matter in which there are illustrated exemplary embodiments of the disclosed technology.

BRIEF DESCRIPTION OF THE DRAWINGS

Illustrative embodiments of the disclosed technology are described in detail below with reference to the attached drawing figures, which are incorporated by reference herein and wherein.

DETAILED DESCRIPTION

Analytical laboratory operations are fast paced, technically complex environments that present numerous challenges for those tasked with their functioning. Challenges exist in maintaining control of the functionality as well as the calibration of the equipment to ensure proper quality control of the testing outcomes. Moreover, the increasing complexity of the laboratory environment creates challenges for finding and retaining personnel with the requisite skill sets. Consequently, there is a need to simplify, or at least not to substantially increase, the complexity of the laboratory operations in order to facilitate human oversight and intervention as appropriate. The obvious goal of such a system is to minimize the amount of human interaction needed within the laboratory operations so that sample analysis may proceed at an optimal rate to maximize throughput yet maintain the highest achievable quality of analytical testing possible.

Tools to increase the productivity of the laboratory environment are already widely available and include, for example, the Atellica™ Process Manager 1.0 Software. The Atellica™ software is a process management tool that simplifies the management of laboratory operations. With this software, laboratory personnel can from one screen manage alerts, remotely control instruments and monitor testing progress and onboard inventory. Combining process management software, such as previously detailed, with augmented reality technology to facilitate management of for example real time alerts or to track STAT samples, is disclosed herein.

Laboratory Monitoring Apparatus

The laboratory monitoring apparatus 10, as disclosed herein, includes an augmented video display for use with a laboratory environment 14 that includes a multitude of diagnostic apparatus 16. The monitoring apparatus 10 includes an image capture device 18 for selectively capturing an optical image 20 of at least a portion of the laboratory environment 14 as well as an image transmission device 22. The image transmission device 22 is in communication with the image capture device 18, for selectively transmitting the captured optical image 20 over a communications medium 26.

The monitoring apparatus 10 also includes an image receiver 30, in communication with the image transmission device 22 via the communications medium 26, for receiving the transmitted optical image 20 from the image transmission device 22. The monitoring apparatus 10 also utilizes an image display device 34 and an image processor 36 in communication with the image receiver 30 and the image display device 34, for selectively generating a display of at least a portion of the captured optical image 20 on the image display device 34.

Figure 1:
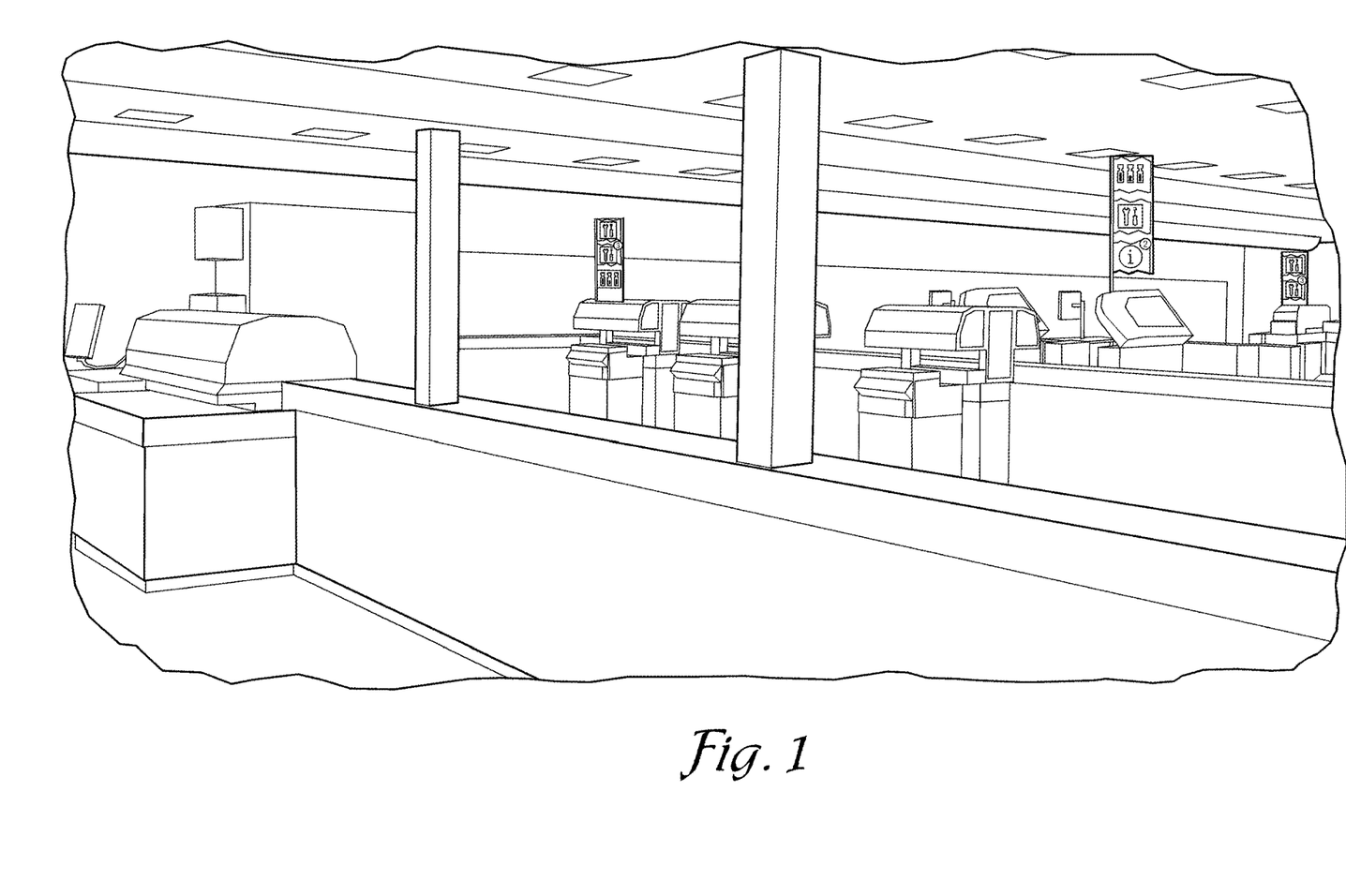
FIG. 1 is view of a portion of a laboratory environment as seen on the display with a graphical rendering identifying the location of the equipment and status.

The monitoring apparatus 10 also includes a laboratory manager 42 in communication with the multitude of diagnostic apparatus 16 at least for receiving status information 44 therefrom and for selectively directing the image processor 36 to embed a rendered graphical element 46 within the generated display 34 in response to the status information 44. FIG. 1 provides an exemplary view of several rendered graphical elements 46 embedded onto the generated display 34 of several items of diagnostic equipment 16 located within the laboratory environment 14. The graphical element 46 is for communicating status information 44 regarding one or more of the plural diagnostics apparatus 16 within the laboratory environment 14 to a user 50 viewing the display 52 on the image display device 34.

The image capture device 18 disclosed herein is preferably a video camera and the optical image 20 is a real time video image of at least a portion of the laboratory environment 14. The image processor 36 selectively displays at least a temporal portion of the optical image 20 on the image display device 34. The image processor 36 is utilized to display the real time video image 20 on the image display device 34. The image processor 36 is used to embed the rendered graphical element 46 in response to selective direction from the laboratory manager 42. The resulting image 52 displayed on the image display device 34 comprises at least a portion of the captured optical image 20 and the rendered graphical element 46.

Figure 2:
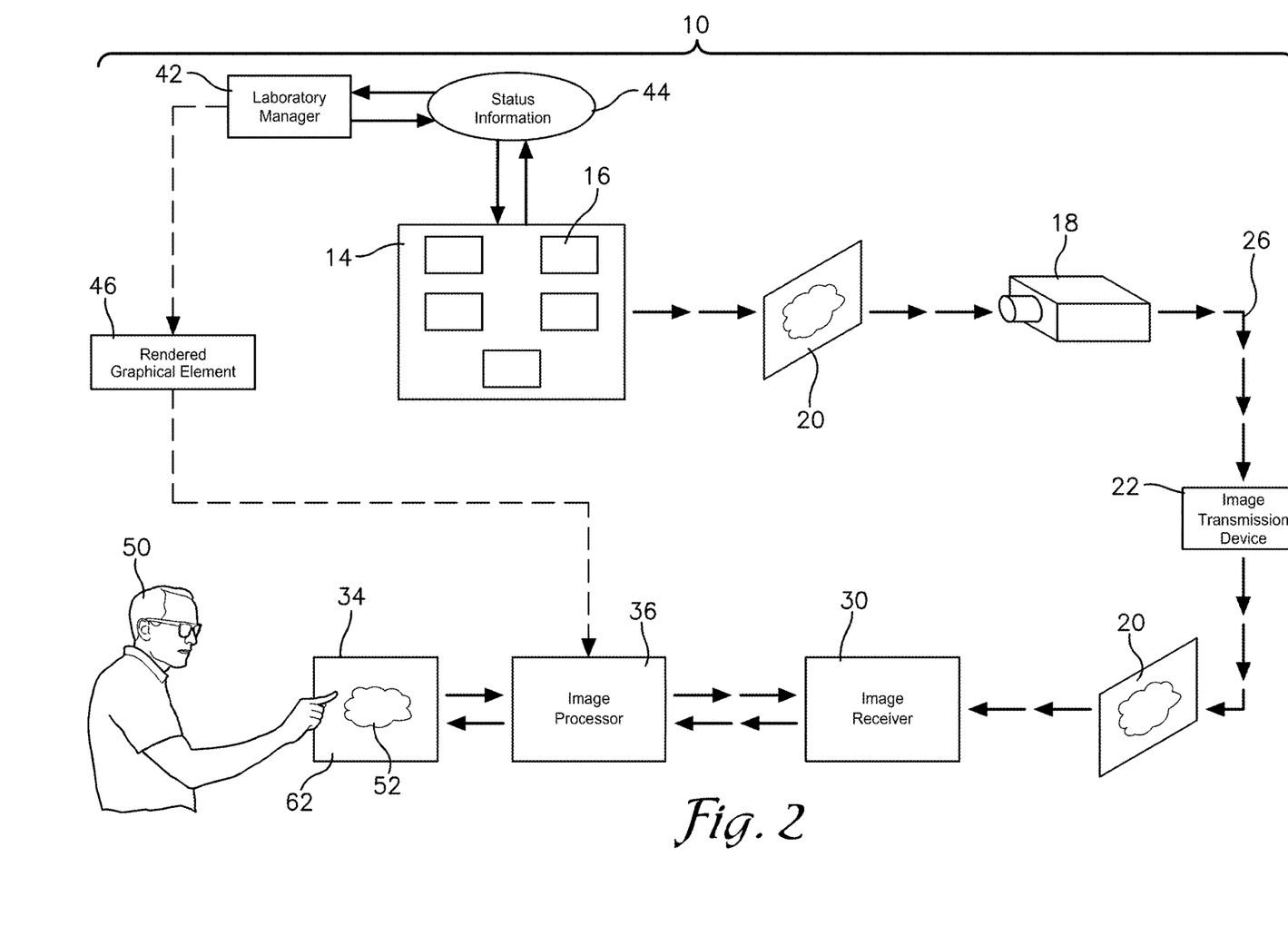
FIG. 2 is a graphical flowchart of the laboratory monitoring apparatus with augmented video display for use with a laboratory environment having plural diagnostic apparatus as disclosed herein.
Figure 3:
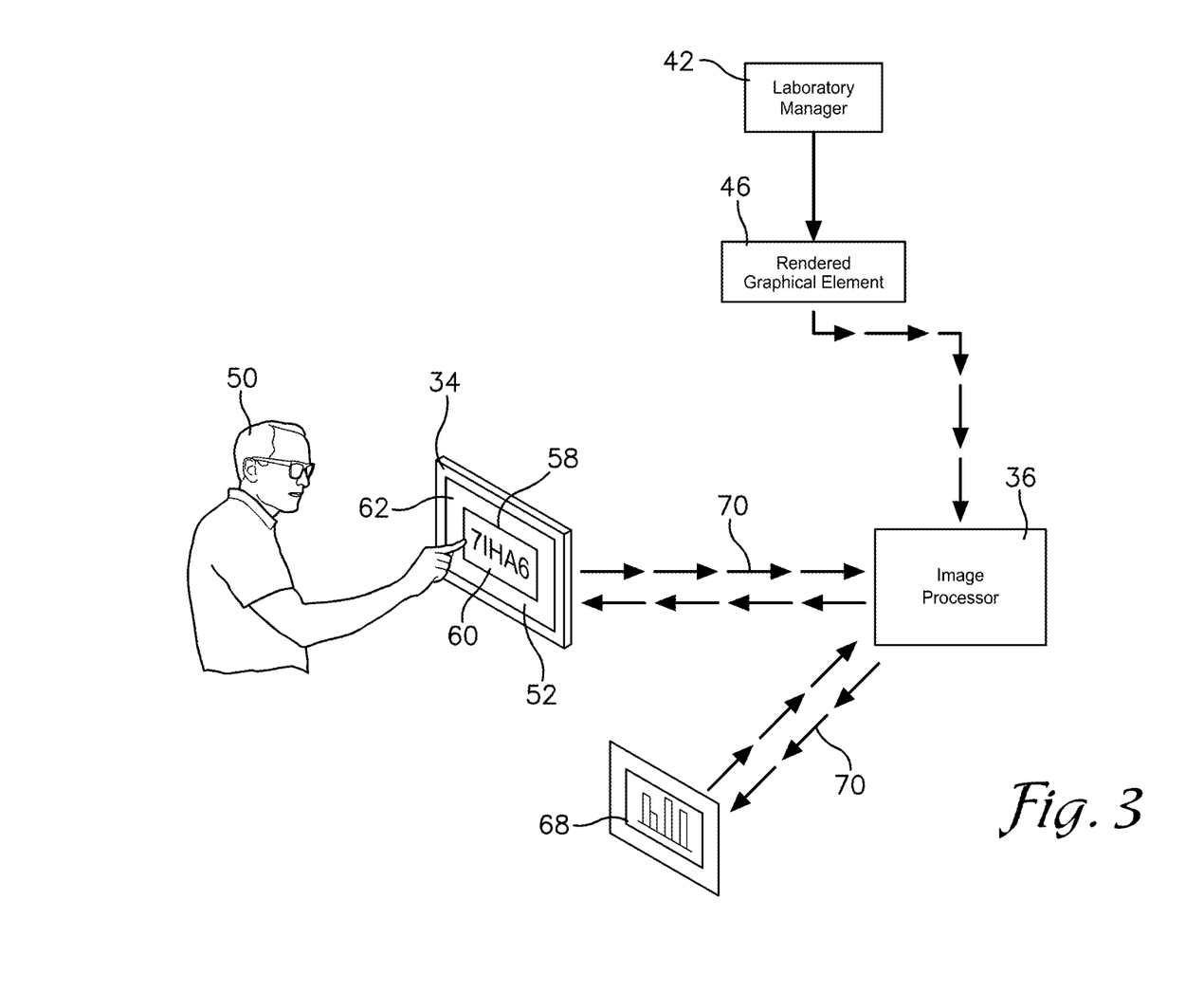
FIG. 3 is a graphical flowchart of a portion of FIG. 1 revealing additional detail on data flow between components.

As previously noted, the image processor 36 is for embedding the rendered graphical element 46 in response to selective direction from the laboratory manager 42. The embedding is accomplished by superimposing the rendered graphical element 46 on at least a portion of the captured optical image 20. As seen in FIG. 2, the image processor 36 embeds the rendered graphical element 46 in response to selective direction from the laboratory manager 42. The rendered graphical element 46 comprises, for example, alphanumerical data 60 associated with at least one of the multitude of diagnostic apparatus 16 of the laboratory environment 14. For example, an osmometer may be one of the diagnostic apparatus 16 in the laboratory environment 14 that is used to make a plasma osmolality determination. As seen in FIG. 3, data from the osmometer alerts the laboratory manager 42 of a low reagent level which in-turn relays the rendered graphical element 46 to the image display device 34. As further seen in FIG. 3, the image processor 36 may also serve to embed the rendered graphical element 46 in response to selective direction from the laboratory manager 42 as a graphical status indicator 61, such as a low reagent level, associated with at least one of the multitude of diagnostic apparatus 16 of the laboratory environment 14.

The image display device 34 comprises a touch sensitive screen 62, whereby a user 50 may interact with the rendered graphical element 46 via the touch sensitive screen 62. The image processor 36 is further for receiving user input 64 via the touch sensitive screen 62 of the image display device 34 and for correlating the user input 64 with a contemporaneous selectively generated display 68. The image processor 36 is further for conveying data 70 indicative of a portion of the contemporaneous selectively generated display 68 to which the user input 64 was correlated to the laboratory manager 42. The laboratory manager 42 is also for communicating with at least one of the multitude of diagnostic apparatus 16 according to the conveyed data 70 from the image processor 36.

Method of Operation

Figure 4:
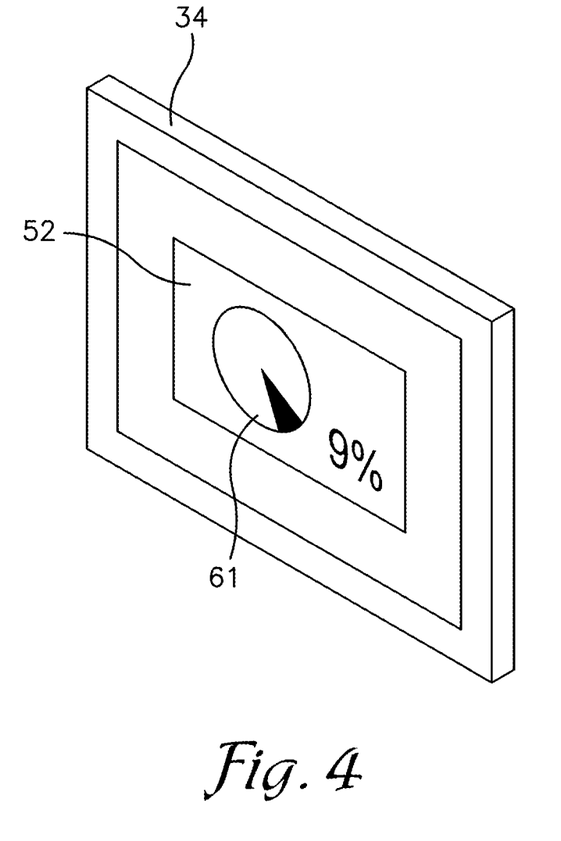
FIG. 4 is a view of the image display device revealing a displayed image and graphical status indicator.
Figure 5:
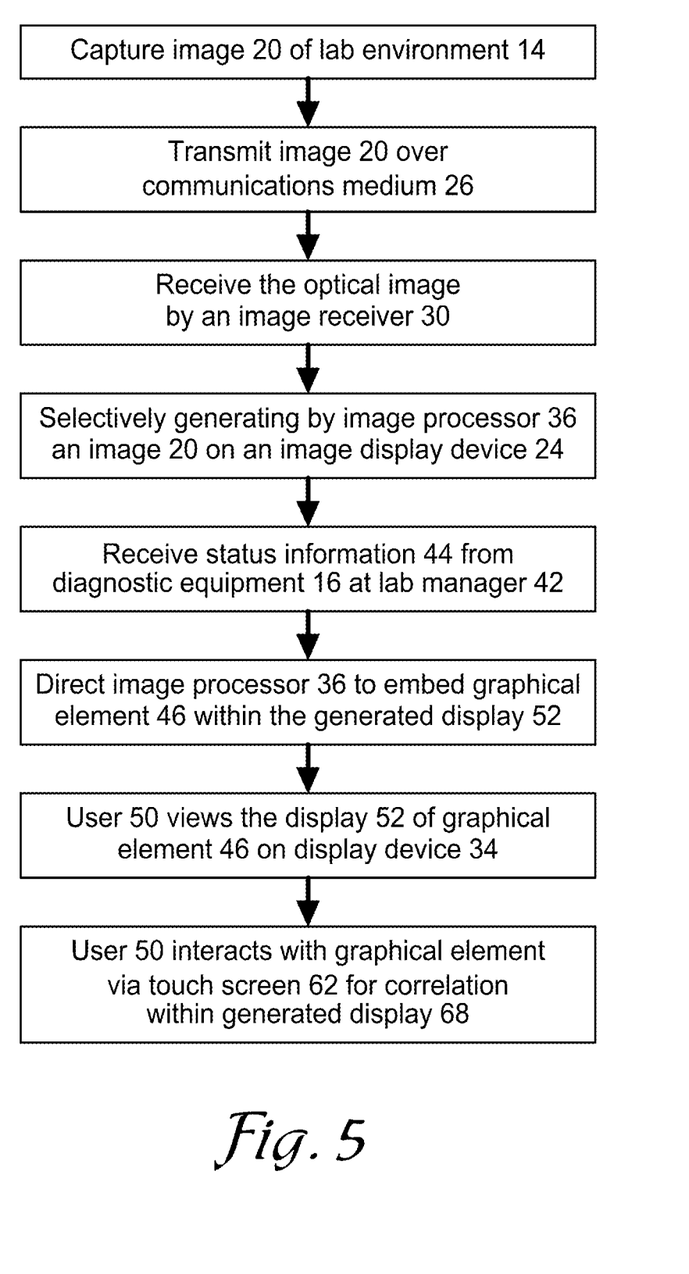
FIG. 5 is a flow chart of the method disclosed herein for the laboratory monitoring apparatus with augmented video display for use with a laboratory environment having a plurality of diagnostic apparatus.

Disclosed herein, and as disclosed in FIG. 4 is a method of enabling supervision of a laboratory environment 14 having a plurality of diagnostic apparatus 16. The method disclosed includes utilization of the image capture device 18 for capturing an optical image 20 of at least a portion of the laboratory environment 14. The method further requires selectively capturing the optical image 20 using the image capture device 18 and selectively transmitting the captured optical image 20 over a communications medium 26 by an image transmission device 22 in communication with the image capture device 18.

The method next requires receiving the transmitted optical image 20 by an image receiver 30 in communication with the image transmission device 22 via the communications medium 26. The method then requires selectively generating, by an image processor 36 in communication with the image receiver 30, a display of at least a portion of the captured optical image 20 on an image display device 24. The method further includes receiving status information 44 from the diagnostic equipment 16 at a laboratory manager 42 that is in communication with the multitude of diagnostic equipment.

The method further requires selectively directing the image processor 36, by the laboratory manager 42, to embed a rendered graphical element 46 within the selectively generated display 52 in response to the received status information 44. The graphical element 46 is used for communicating status information relating to one or more of the plural diagnostics apparatus 16 within the laboratory environment to a user 50 viewing the display 52 on the image display device 34.

In the method disclosed herein, the optical image 20 is a real time video image of at least a portion of the laboratory environment 14 and the image processor 36 selectively displays at least a temporal portion of the optical image 20 on the image display device 34. The image processor 36 also embeds the rendered graphical element 46, whereby the image displayed on the image display device comprises at least a portion of the captured optical image 20 and the rendered graphical element 46. The image processor 36 is capable of embedding the rendered graphical element 46 by superimposing the rendered graphical element on at least a portion of the captured optical image 20. In operation, the image processor 36 selectively embeds the rendered graphical element 46 comprising alphanumeric data 60 associated with at least one of the diagnostic apparatus 16 in the laboratory environment 14.

Next, the image processor 36 selectively embeds the rendered graphical element 46 as a graphical status indicator 61 associated with at least one of the plurality of diagnostic equipment 16 in the laboratory environment 14. The image display device 34 comprises a touch sensitive screen 62. A user 50 interacts with the rendered graphical element 46 via the touch sensitive screen 62. The image processor 36 receives user input via the touch sensitive display 62 of the image display device 34 and correlates the user input with a contemporaneous selectively generated display 68.

The method disclosed herein further requires the conveyance of data 70 indicative of a portion of the contemporaneous selectively generated display 68 to which the user input 64 was correlated to the laboratory manager 42. The laboratory manager 42 communicates with at least one of the diagnostic equipment 16 according to the conveyed data 70 from the image processor 36.

Many different arrangements of the various components depicted, as well as components not shown, are possible without departing from the spirit and scope of the disclosed technology. Embodiments of the disclosed technology have been described with the intent to be illustrative rather than restrictive. Alternative embodiments will become apparent to those skilled in the art that do not depart from its scope. A skilled artisan may develop alternative means of implementing the aforementioned improvements without departing from the scope of the disclosed technology.

It will be understood that certain features and sub combinations are of utility and may be employed without reference to other features and sub combinations and are contemplated within the scope of the claims. Not all steps listed in the various figures need be carried out in the specific order described.

I claim:

1. A laboratory monitoring apparatus with augmented video display for use with a laboratory environment having plural diagnostic apparatus, comprising:
    an image capture device for selectively capturing an optical image of at least a portion of the laboratory environment, the captured optical image of the laboratory environment comprising a plurality of diagnostic apparatus;
    an image transmission device, in communication with the image capture device, for selectively transmitting the captured optical image over a communications medium;
    an image receiver, in communication with the image transmission device via the communications medium, for receiving the transmitted optical image from the image transmission device;
    an image display device; and
    an image processor, in communication with the image receiver and the image display device, for selectively generating a display of at least a portion of the captured optical image on the image display device, for receiving user input via a touch sensitive screen of the image display device, and for correlating the user input with a respective portion of the contemporaneous selectively generated display to generate correlated display data; and
    a laboratory manager in communication with at least one of the plural diagnostic apparatus, at least for receiving operating status information therefrom, and the image processor, at least for receiving the correlated display data conveyed by the image processor, for selectively directing the image processor to embed a rendered graphical element within the generated display identifying the precise location of one or more of the plural diagnostic apparatus within the laboratory environment in response to the received status information and the received correlated display data, wherein the graphical element is embedded in the portion of the captured optical image in proximity to the one or more of the plural diagnostic apparatus shown in the portion of the captured optical image, the graphical element for communicating (a) alphanumeric operating status information, and (b) location information regarding one or more of the plural diagnostics apparatus within the laboratory environment to a user viewing the display on the image display device, and for communicating with the at least one of the plural diagnostic apparatus according to the correlated conveyed data from the image processor.

2. The laboratory monitoring apparatus of claim 1, wherein:
    the image capture device is a video camera; and
    the optical image is a real-time video image of at least a portion of the laboratory environment.

3. The laboratory monitoring apparatus of claim 2, wherein the image processor is for selectively displaying at least a temporal portion of the optical image on the image display device.

4. The laboratory monitoring apparatus of claim 2, wherein the image processor is for displaying the real-time video image on the image display device.

5. The laboratory monitoring apparatus of claim 1, wherein the image processor is for embedding the rendered graphical element in response to selective direction from the laboratory manager, whereby the image displayed on the image display device comprises at least a portion of the captured optical image and the rendered graphical element.

6. The laboratory monitoring apparatus of claim 5, wherein the image processor is for embedding the rendered graphical element in response to selective direction from the laboratory manager by superimposing the rendered graphical element on at least a portion of the captured optical image.

7. The laboratory monitoring apparatus of claim 1, wherein the image processor is for embedding the rendered graphical element in response to selective direction from the laboratory manager as a pop-up window comprising alphanumerical data associated with at least one of the plural diagnostic apparatus of the laboratory environment.

8. The laboratory monitoring apparatus of claim 1, wherein the image processor is for embedding the rendered graphical element in response to selective direction from the laboratory manager as a graphical status indicator associated with at least one of the plural diagnostic apparatus of the laboratory environment.

9. A method of enabling supervision of a laboratory environment having plural diagnostic apparatus, comprising:
    disposing an image capture device for capturing an optical image of at least a portion of the laboratory environment to include a plurality of diagnostic apparatus;
    selectively capturing the optical image using the image capture device;
    selectively transmitting the captured optical image over a communications medium by an image transmission device in communication with the image capture device;
    receiving the transmitted optical image by an image receiver in communication with the image transmission device via the communications medium;
    selectively generating, by an image processor in communication with the image receiver, a display of at least a portion of the captured optical image on an image display device;

selectively receiving, by the image processor, user input via a touch sensitive screen of the image display device and correlating, by the image processor, the user input with a respective portion of the contemporaneous selectively generated display to generate correlated display data;

receiving operating status information, from at least one of the plural diagnostic apparatus, and the correlated display data, conveyed by the image processor, at a laboratory manager in communication therewith;

selectively directing the image processor, by the laboratory manager, to embed a rendered graphical element within the selectively generated display identifying the precise location of one or more of the plural diagnostic apparatus in response to the received status information and the received correlated display data, wherein the graphical element is embedded in the portion of the captured optical image in proximity to the one or more of the plural diagnostic apparatus shown in the portion of the captured optical image, the graphical element for communicating (a) alphanumeric operating status information, and (b) location information relating to one or more of the plural diagnostics apparatus within the laboratory environment to a user viewing the display on the image display device; and communicating, by the laboratory manager, with the at least one of the plural diagnostic apparatus according to the correlated conveyed data from the image processor.

10. The method of claim 9, wherein:
the image capture device is a video camera; and
the optical image is a real-time video image of at least a portion of the laboratory environment.

11. The method of claim 10, wherein the image processor selectively displays at least a temporal portion of the optical image on the image display device.

12. The method of claim 10, wherein the image processor displays the real-time video image on the image display device.

13. The method of claim 9, wherein the image processor embeds the rendered graphical element, whereby the image displayed on the image display device comprises at least a portion of the captured optical image and the rendered graphical element.

14. The method of claim 13, wherein the image processor embeds the rendered graphical element by superimposing the rendered graphical element on at least a portion of the captured optical image.

15. The method of claim 9, wherein the image processor selectively embeds the rendered graphical element as a pop-up window comprising alphanumeric data associated with at least one of the plural diagnostic apparatus of the laboratory environment.

16. The method of claim 9, wherein the image processor selectively embeds the rendered graphical element as a graphical status indicator associated with at least one of the plural diagnostic apparatus of the laboratory environment.

* * * * *